United States Patent [19]
Bruce et al.

[11] Patent Number: 5,756,789
[45] Date of Patent: May 26, 1998

[54] SYNTHESIS OF METAL—CONTAINING ALUMINOPHOSPHATES WITH LAYERED STRUCTURE

[75] Inventors: David Alan Bruce, Douglasville; Mark Gilmore White, Woodstock; Joseph Aaron Bertrand, Atlanta, all of Ga.; Pei-Shing Eugene Dai, Port Arthur; Randall Hughes Petty, Port Neches, both of Tex.

[73] Assignee: Texaco, Inc., White Plains, N.Y.

[21] Appl. No.: 659,977

[22] Filed: Jun. 3, 1996

Related U.S. Application Data

[60] Provisional application No. 60/000,049, Jun. 8, 1995, and No. 60/000,069, Jun. 8, 1995.

[51] Int. Cl.$^6$ .............................. C07F 15/06; C07F 5/06; C07F 9/02
[52] U.S. Cl. ........................ 556/14; 502/213; 502/414; 502/439; 556/28; 556/174
[58] Field of Search ........................ 556/14, 28, 174; 502/414, 439, 213

[56] References Cited

U.S. PATENT DOCUMENTS

| | | | |
|---|---|---|---|
| 3,941,871 | 3/1976 | Dwyer et al. | 423/326 |
| 4,259,306 | 3/1981 | Pelrine | 423/325 |
| 4,310,440 | 1/1982 | Wilson et al. | 252/435 |
| 4,338,385 | 7/1982 | Eberts | 422/257 |
| 4,500,503 | 2/1985 | Rankel et al. | 423/329 |
| 4,568,654 | 2/1986 | Valyocsik | 502/62 |
| 5,051,246 | 9/1991 | Clark et al. | 423/305 |
| 5,102,642 | 4/1992 | Clark et al. | 423/328 |
| 5,167,942 | 12/1992 | Balkus et al. | 423/705 |

*Primary Examiner*—Porfirio Nazario-Gonzalez
*Attorney, Agent, or Firm*—Henry H. Gibson; Carl G. Ries

[57] ABSTRACT

Disclosed is a novel process for the synthesis of a metal-containing aluminophosphate having a layered structure and novel optically active metal-containing aluminophosphates useful as enantio-selective catalysts, which comprises:

a) slurring an aluminum source with water;
b) adding a phosphorus source and slurring;
c) allowing the mixture to stand;
d) adding an organic additive;
e) allowing the mixture to stand;
f) adding a cationic transition metal complex
g) heating to 80°–250° C. for 20–180 hours wherein the mole ratio of transition metal complex to organic additive is in the range of 0.1–1.0:1.0.

15 Claims, 1 Drawing Sheet

SYNTHESIS OF METAL— CONTAINING ALUMINOPHOSPHATES WITH LAYERED STRUCTURE

CROSS REFERENCE

This Application is a continuation-in-part of U.S. Provisional application Ser. Nos. 60/000,049 and 60/000,069, filed Jun. 8, 1995.

FIELD OF THE INVENTION

The present invention relates to a novel family of aluminophosphates and to a method for their synthesis. More particularly it relates to a method for using cationic transition metal complexes as co-templates in the synthesis of a novel aluminophosphate composition. The resulting catalyst composition is useful for catalyzing the selective oxidation of hydrocarbons, such as, for example, the hydroxylation of phenol with hydrogen peroxide to form hydroquinone and catechol. The catalyst composition can also be produced in an optically active form which may act as an enantioselective catalyst for the production of chiral compounds, as an absorbent, or as a catalyst for the separation of racemic mixtures.

BACKGROUND OF THE INVENTION

In 1982 AlPO$_4$ molecular sieves were first reported by Wilson et al. in U.S. Pat. No. 4,310,440. Before this time molecular sieves of the crystalline zeolite type were well known in the art and over 150 species of both naturally occurring and synthetic compositions were known. In general the crystalline zeolites are aluminosilicates where the frameworks are formed from AlO$_4$ and SiO$_4$ tetrahedra joined by the sharing of oxygen atoms and characterized by having pore openings of uniform dimensions, having a significant ion-exchange capacity and capable of reversibly desorbing an adsorbed phase which is dispersed through the internal voids of the crystal without displacing any atoms which make up the permanent crystal structure.

Other crystalline microporous phases which were not zeolite were also known. They did not contain the AlO$_4$-tetrahedra as essential framework constituents, but exhibited the ion exchange and/or adsorption characteristics. Among these were metallorganosilicates, reported in U.S. Pat. No. 3,941,871, and a pure silica polymorph having molecular sieving properties and a neutral framework.

Since the disclosure of aluminophosphates in U.S. Pat. No. 4,310,440, a large family of novel crystalline aluminophosphate (AlPO$_4$) based molecular sieves has been discovered and has been described in the literature.

See: E. M. Flanigen, B. M. Lok, S. T. Wilson, in "New Developments in Zeolite Science and Technology", Proceeding of the 7th International Zeolite Conference Edited by Y. Murakami, A. Iijima and J. W. Ward; Elsevier, New York, 1986, p. 103;

E. M. Flanigen, R. L. Patton, S. T. Wilson, in "Innovation in Zeolite Materials Science", P. J. Grobet et al., Eds.; Stud. Surf. Sci. Catal., 37, 13 (1988); and B. M. Lok, C. A. Messina, R. L. Patton, and E. M. Flanigen, J. Am. Chem. Soc., 106, 6092 (1984).

The major structures crystallized in the new generations of AlPO$_4$-based molecular sieves include at least 30 stable three-dimensional novel structures. Some are topological analogs of zeolites such as faujasite, A, chabazite, and erionite. The structures include large-pore (7–8 Å), medium-pore (6 Å), and small-pore (3–4 Å) materials.

The materials are classified into binary, ternary, and quaternary compositions based on the number of elements contained in the cationic framework sites of any given structure. Classes of these materials comprise compositions crystallized in the AlPO$_4$, silicoaluminophosphates (SAPO), metal aluminophosphates (MeAPO) and non-metal element incorporated aluminophosphates (ElAPO) families. A summary of typical compositions and structures crystallized in the AlPO$_4$, SAPO, MeAPO and MeAPSO families of compositions is given in Table 3, and in the ElAPO and ElAPSO families in Table 4, in the reference article entitled "Aluminophosphate Molecular Sieves and the Periodic Table".

The AlPO$_4$ molecular sieves exhibit an invariant framework composition with an Al/P atomic ratio of 1 and a wide structural diversity. Their product composition expressed as an oxide formula, is $xR.Al_2O_3.1.0\pm0.2P_2O_5.yH_2O$, where R is an amine of a quaternary ammonium template, and x, and y represent the amounts needed to fill the microporous voids. Upon calcination at temperatures of 773–873K, the molecular sieves are expressed as AlPO$_4$ or a TO2 formula of $(Al_{0.50}P_{0.50})O_2$. The microporous AlPO$_4$ materials have novel structures, 5, 11, 14, 16, 18, 31, and 33. For example, the as-synthesized AlPO$_4$-11 has a typical composition of 1.0 Pr$_2$NH: 1.0 Al$_2$O$_3$:1.0 P$_2$O$_5$: 40 H$_2$O, and consists of an open framework containing unidimensional 10-ring channels (3.9×6.3 Å).

The silicoaluminophosphates (SAPO) are made by the substitution of silicon for phosphorus and with some substitution of two silicons for an aluminum plus phosphorus into a hypothetical aluminophosphate framework. The general formula of the anhydrous SAPO composition is 0–0.3 R $(Si_xAl_yP_z)O_2$ where the mole fraction of silicon, x, typically varies from 0.04 to 0.20 depending on synthesis conditions and structure type. The typical SAPO-11 framework composition is $(Si_{0.14}Al_{0.44}P_{0.42})O_2$ with (x+z) greater than y.

In the MeAPO family, the framework composition contains metal, aluminum and phosphorus. The metal (Me) species include the divalent forms of Co, Fe, Mg, Mn, and Zn, and trivalent Fe. As in the case of SAPO, the MeAPO molecular sieves exhibit a wide range of compositions with the general formula, 0–0.3 R $(Me_xAl_yP_z)O_2$. The value of x, the mole fraction of Me, typically varies from 0.01 to 0.25. The typical MeAPO-11 framework composition is $(Me_{0.08}Al_{0.42}P_{0.50})O_2$ with (x+z) greater than y. In contrast to the mechanism observed for SAPO's, in the MeAPO's the metal appears to substitute exclusively for Al rather than P. This mode of substitution, divalent or trivalent metal for trivalent Al, results in a net negative ($Me^{2+}$) or neutral ($Me^{3+}$) framework charge. Like SAPO, the negatively charged MeAPO frameworks possess ion exchange properties and the potential for Bronsted acid sites. The metal in the MeAPO's framework may also change their oxidation state while maintaining their framework positions. Therefore, MeAPO may afford catalytic activity in the oxidation of hydrocarbons.

Aluminophosphate-based molecular sieves are synthesized by hydrothermal crystallization of reactive aluminophosphate gels containing the additional framework elements and an organic template at temperatures from 373 to 573K. Structure control is function of a number of synthesis variables, including template species and concentration, reactant gel composition, element composition, crystallization temperature and time, and pH value. The organic template appears to play a critical role in directing the structure. The degree of template-structure specificity varies widely from the crystallization of AlPO$_4$-5 with twenty-three templates to the formation of AlPO$_4$-20 with only one template. In addition to its structure-directing and space-filling/stoichiometry roles, the organic template can also play an essential role in framework charge compensation. In the AlPO$_4$ materials with neutral frameworks, the template is a cationic species and must be balanced by an extra framework anionic species, most commonly OH$^-$ ions.

In the synthesis of MeAPO molecular sieves, the reactive source of metals is incorporated in the form of metal salts such as cobalt acetate and iron sulfate during the preparation of gel mixtures (e.g. in the synthesis of COAPO and FeAPO-11, EP 0 158 977). There have been reports of zeolite synthesis employing transition metal complexes, but it has not been firmly established that the metal complexes are encapsulated intact within the intrazeolite pores or cages or function as templates. See U.S. Pat. Nos. 4,500,503 and 4,338,285 to Rankel t al., and U.S. Pat. No. 4,259,306 to Pelrine.

In U.S. Pat. No. 4,568,654 E. W. Valyocsik discloses the se of bis(cyclopentadienyl) cobalt (III) hexafluorophosphate, Cp$_2$CoPF$_6$ as a template for the hydroxide synthesis of ZSM-51 zeolite which has the nonasil (NON) topology.

In U.S. Pat. No. 5,167,942, Balkus et al. demonstrate that several first row transition metal phthalocyanine complexes can be encapsulated in X and A type zeolites by synthesizing the zeolite around the metal complex. The synthesis of X and A type zeolites does not require an organic template, however, the metal complexes appears to modify the gel chemistry. Therefore the addition of metal complexes not only provides a method for lo preparing intrazeolite metal complexes but also may influence the crystal structure of molecular sieves.

Also see "Zeolite Chemistry and Catalysis" ed. by P. A. Jacobs et al., Stud. Surf. Sci. Catal., 69, 93 (1991).

In Inorg. Chem., 32, 5029, (1993), Kraushaar-Czarnetzki et al. report the synthesis and structure of SCS-22, the first member of a novel family of aluminophosphates. SCS-22 exhibits a layered structure intercalated by straight-chain alkylenediamines which are added to the synthesis gel like a "template". Both Al and P are tetrahedrally coordinated and can be isomorphously substituted (e.g. Co for Al and Si for P) as in AlPO$_4$-based molecular sieves. The Co atoms in the samples of CoAPSO-SCS-22 are in the framework of TO$_2$ tetrahedra. The general formula proposed for CoAPSO-SCS-22 compounds is denoted as R$_{1.5}$[Al$_{3-x}$Co$_x$H$_{3+x+y}$(PO$_4$)$_{4-y}$(SiO$_4$)$_y$] where R represents a diamine H$_2$N(CH$_2$)$_n$NH$_2$ with n≧8.

U.S. Pat. Nos. 5,051,246 and 5,102,642 disclose the preparation of novel crystalline aluminophosphates having in the as-synthesized anhydrous form a composition: mR(X$_n$Al$_q$P$_x$)O$_2$ wherein m=0.01–0.33, n=0–0.40, q=0.30–0.60, x=0.30–0.60 and n+q+x=1 and wherein X can be Ni, Mn, Fe, Co, and Zn.

In Zeolites, 11, 612 (1991), N. Rajic et al. reported the preparations of NiAPO-12 and NiAPO-21 using ethylenediamine (en) as a template. Ni(II) in NiAPO-21 is octahedrally coordinated and interacts with water and ethylenediamine molecules.

Cobalt-containing aluminophosphates (COAPO) and ferroaluminophosphate molecular sieves (FAPO) have received much attention. The redox character of framework cobalt in these materials has been demonstrated by using reducing agents such as H$_2$ and NO. J. W. Part and H. Chen, J. Catal., 133, 159 (1992).

Recently Sheldon et al. found that CoAPO-5 and CoAPO-11 are stable, recyclable catalysts for the selective oxidation of p-cresol to p-hydroxybenzaldehyde, with molecular oxygen in alkaline methanolic solution at 50° C. See J. Dakka and R. A. Sheldon, Netherland Patent Appl., 920968 (1992).

The synthesis of a heterogenous enantio-selective catalysts is considered one of the major hurdles required for the synthesis of desirable new catalysts for the production of specialty chemicals. One method of preparing a chiral molecule involves the addition of a chiral compound into the cages of a zeolite. The alternative method is to synthesize a chiral solid. The number of chiral solids that can perform enantio-selective catalysis is very limited. To our knowledge none of the molecular sieves known to date are chiral solids. Therefore, the synthesis of a chiral MeAPO would be a great advance in the art. H. U. Blaser and M. Muller, Stud. Surf. Sci. and Catal., 59, Elsevier, 1991, pp 73–92.

In U.S. Pat. No. 4,310,440, there is disclosed a novel family of crystalline, microporous aluminophosphates compositions synthesized by hydrothermal crystallization at elevated temperatures of aluminophosphate gels containing a molecular structure-forming template. The crystalline material exhibits uniform pore sizes of about 3 Å to 10 Å and comprises a new class of absorbents of the molecular sieve type.

U.S. Pat. No. 4,500,503 discloses an improvement in a process for the synthesis of mordenite which comprises adding a metal complex having stability at relative high pH to the reaction mixture to utilize as a template for the synthesis of mordenite type zeolites.

In U.S. Pat. No. 4,259,306, there is disclosed a method for synthesizing zeolite ZSM-39 in the presence of pyrrolidine as a template rather than the template of a tetraethylammonium cation or m-propylamine.

In U.S. Pat. No. 4,568,654, there is disclosed a method of preparation and use for a novel crystalline zeolite identified as ZSM-51.

U.S. Pat. No. 5,167,942 discloses an improved method for the preparation of aluminum phosphate molecular sieves and faujasite-type zeolites having stably encapsulated multidentate metal chelate complexes which is achieved through direct incorporation of a selected multidentate chelate complex into the molecular sieve or zeolite reaction admixture prior to crystallization.

In U.S. Pat. No. 5,051,246, there is disclosed crystalline aluminophosphates having an as-synthesized anhydrous form with the chemical composition: n'R(X$_n$Al$_q$P$_x$)O$_2$, where R represents 1,3-diaminopropane, x represents one or more elements which can be substituted for Al and/or P and n', n, q, and x have specific ranges.

U.S. Pat. No. 5,102,642 discloses a composition which appears similar to that of U.S. Pat. No. 5,051,246, supra but has a greater number of possible x-ray diffraction patterns.

Morgan, K. et al. have reported the synthesis and structure of a novel layered aluminum phosphate formed about a chiral metal complex. See A Novel Layerd Aluminum Phosphate [Co(en)$_3$Al$_3$P$_4$O$_{16}$·3H$_2$O] assembled about a chiral metal complex. J. Chem. Soc. Chem. Commun., 1995, p. 425–426.

There is a need in the art for a method of synthesizing MeAPO materials using a transition metal complex as the structure directing template. Compositions of this type should possess unique structural, and catalytic properties. It would be particularly desirable if it were possible to synthesize an optically active metal-containing aluminophosphate. Such a composition should be a very valuable catalyst for the production of fine chemicals. It should act as an enantio-selective catalyst for the production of chiral compounds and could also be used as an absorbent for the separation of racemic mixtures. A method for synthesizing such a catalyst would definitely represent a tremendous advance in the art.

SUMMARY OF THE INVENTION

In accordance with the foregoing the present invention comprises the synthesis of a metal-containing aluminophosphate composition useful as a catalyst in the reaction of phenol with hydrogen peroxide to form hydroquinone and catechol, as well as in a number of other reactions, said compositions represented by the general formula:

$M.Al_3P_4O_{16}.nH_2O$ where M is a transition metal complex having a +1, +2, or +3 charge, preferably a transition metal amine complex, and n=0-2.

Using the method of this invention the metal-containing aluminophosphate composition can also be synthesized in a optically active form.

DETAILED DESCRIPTION OF THE INVENTION

The present invention discloses the synthesis of a family of novel metal-containing aluminophosphates having a layered structure employing both a transition metal complex and an organic additive as the structure-directing agents. The composition of this family of novel aluminophosphates, in the as-synthesized form can be expressed by the general formula $M.Al_4P_4O_{16}.nH_2O$ wherein M is a transition metal complex ion having +1 or +2, or +3 charge, preferably a transition metal amine complex, and n=0-2.

These aluminophosphate compositions are synthesized using transition metal amine or aminoalcohol complexes as a source of metals in a method for synthesizing metal-containing aluminophosphates comprising:
a) slurring an aluminum source with water;
b) adding a phosphorus source and stirring;
c) allowing the mixture to stand;
d) adding an organic additive;
e) allowing the mixture to stand;
f) adding a cationic transition metal complex;
g) heating to 80°–250° C. for 20–180 hours
wherein the mole ratio of transition metal complex to organic additive is in the range of 0.1–1.0:1.0.

It is believed that the transition metal complexes modify the structure-directing effect of organic templates on the zeolite crystallization.

The novel aluminophosphate materials are herein labeled GTex-1 and are, for example, active catalysts for the hydroxylation of phenol with hydrogen peroxide, demonstrating high selectivity for hydroquinone.

In synthesis of the novel aluminophosphate, the preferred aluminum source is either an aluminum alkoxide, such as aluminum isopropoxide or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed, but are not preferred.

The most suitable phosphorus source found for the present method is a phosphoric acid. The most preferred is orthophosphoric. Organic phosphates such as triethylphosphate may be (have been found) satisfactory, and so also have crystalline or amorphous aluminophosphates such as the AlPO$_4$ composition of U.S. Pat. No. 4,310,440 organophosphorous compounds, such as tetrabutylphosphonium bromide do not, apparently serve as reactive sources of phosphorus. Conventional phosphorus salts, such as sodium metaphosphate, could be used, but are not preferred.

The organic additives suitable for use as a structure-directing or templating agent in the synthesis include dipropylamine (DPA), tripropylamine (TPA), tetramethylammonium hydroxide (TMA), and tetrabutyl ammonium hydroxide (TBA).

The ligands of transition metal complexes used as the structure-directing template in the synthesis of novel MeAPO materials are nitrogen-containing molecules having bidentate or tridentate functionalities. The preferred ligands are ethylenediamine (en), diethylenetriamine (dien), and trimethylenediamine (tn) and suitable metals include, but are not limited to cobalt, nickel, iron, manganese and molybdenum. Specific examples of transition metal complexes are Co(en)$^{3+}$,en: ethylenediamine; and Co(DAPO)$_2$. DAPO is diaminoisopropoxide.

The present invention is extremely valuable in that we have now discovered that highly crystalline aluminophosphate materials containing the optically active d-Co(en)$^{3+}$ diastereo-isomer can be synthesized. This is accomplished using the contemplating agent or pH adjustment material, such as an amine or alkylammonium hydroxide, along with the optically active dextro isomer of a transition metal complex.

In the embodiment for synthesizing the optically active composition, the transition metal complexes are isomers or dextro isomers of transition metal complexes. Examples include, but are not limited to, the dextro isomer of cobalt (III) trisethylenediamine chloride, the isomer of cobalt (III) bisdiethylenetriamine chloride, the isomer of cobalt (III) tristrimethylenediamine chloride.

The present aluminophosphates are prepared by crystallization of a reaction mixture prepared by slurring the source of alumina in water and adding to this slurry a source of phosphoric acid in water. This mixture is stirred for about 5 minutes and allowed to stand at ambient conditions for 12–24 hours without agitation. To this mixture is then added a 25% aqueous solution of chelating agent and the mixture is again allowed to stand for 12–24 hours. To the resulting mixture was added transition metal complex for the final reaction mixture.

The molar ratio of the final mixture of organic templating agent: Transition metal Complexes: Al$_2$O$_3$: P$_2$O$_5$: H$_2$O was in the range of 0.5–2: 0.10–1.0:0.5–2; 0.5–2.0: 30–50.

The mixture is placed in a sealed teflon lined stainless steel pressure vessel and heated at 120°–180° C. for 50–100 hrs.

The solid product is recovered by filtration, washed with water, and dried in air at room temperature.

The preferred conditions for synthesizing the novel metal-containing aluminophosphate with layered structure include an aging time of 2–24 hours, crystallization temperature of 110°–200° C., crystallization time of 24–168 hours, and a mole ratio of transition metal complex to organic additive of 0.1–1.0:1.0 the composition of the gel mixture represented by:

mR.nTMC.x $Al_2O_3$.y$P_2O_5$.z$H_2O$, wherein
m=1.0±0.1;n=0.1–1.0; x=1.0±0.1; y=1.0±0.1;
z=40–60; R=organic additive, and TMC=transition metal complex.

The optically active metal-containing aluminophosphates are labeled GTex-n.

Solids showing chirality can be prepared by using a single, optical isomer of the metal complex as the template which is described in the procedure for making GTex-1; GTex-2; or GTex-3. A physical mixture of chiral, single crystals will be produced when using a racemic mixture of the metal complex as the template described in the procedures of GTex-2 and GTex-3. No chiral solid is formed when using a racemic mixture of the metal complex as the template described in the procedure of GTex-1.

The resulting GTex-n material is useful for the production of lo alcohols, ketones, and epoxides from the reaction of alkanes, alkenes, and alkyaromatics with hydrogen peroxide and organic peroxide at mild conditions.

The examples which follow illustrate the preparation of the novel aluminophosphate with layered structure. These examples are only intended as a means of illustration and it should be understood the invention is not meant to be limited thereby.

Examples I through XIV and Tables I through V demonstrate the synthesis and use of the metal-containing aluminophosphate with layered structure, GTex-1, and Examples XV through XIX and Tables VI through IX demonstrate the preparation and use of the novel optically active metal-containing aluminophosphates with layered structure, GTex-n.

EXAMPLE I

Example I (DBAP24) illustrates the best mode of synthesis of GTex-1 with high crystallinity (99%). 5.0 grams of Catapal B alumina (pseudoboehmite) was slurried in 8.5 ml water. To this slurry was added a solution of 9.2 grams of 85% orthophosphoric acid in 8.5 ml water. This mixture was stirred for 5 minutes, and then was allowed to stand at ambient conditions for 12 hours without agitation. To this mixture was added 14.5 grams of 25% aqueous solution of tetramethylammonium hydroxide (TMA). This mixture was allowed to stand at ambient conditions for 12 hours without agitation. To the resulting mixture was added 4.6 grams of cobalt (III) trisethylenediamine chloride, [Co(en)$_3$]Cl$_3$, to form the final reaction mixture. The composition of the final reaction mixture in mole ratio was 1.0 TMA:0.25 [Co(en)$_3$]Cl$_3$:1.0 Al$_2$O$_3$:1.0 P$_2$O$_5$:45 H$_2$O The reaction mixture was placed in a sealed teflon-lined stainless steel pressure vessel and heated at 150° C. for 72 hours. The solid product was recovered by filtration, washed with water, and dried in air at room temperature. A portion of the solid was subjected to X-ray analysis. The solid had an X-ray powder diffraction pattern characterized by the data shown in Tables I-A, I-B and I-C.

EXAMPLE II

This Example (DBAP-3) illustrates the preparation of GTex-1 material with high crystallinity (95%) using dipropylamine as the organic additive. 5.0 grams of Catapal B alumina (pseudoboehmite) was slurried in 15 ml water. To this slurry was added a solution of 9.2 grams of 85% orthophosphoric acid in 12.8 ml water. This mixture was stirred for 5 minutes, and then was allowed to stand at ambient conditions for two hours without agitation. To this mixture was added 4.0 grams of dipropylamine (DPA). To the resulting mixture 4.6 grams of cobalt (III) trisethylenediamine chloride, [Co(en)$_3$]Cl$_3$, complex to form the final reaction mixture. The composition of the final reaction mixture in mole ratio was 1.0 DPA:0.25 [Co(en)$_3$]Cl$_3$:1.0 Al$_2$O$_3$:1.0 P$_2$O$_5$:45 H$_2$O The reaction mixture was placed in a sealed teflon-lined stainless steel pressure vessel and heated at 150° C. for 24 hours. The solid product was recovered by filtration, washed with water, and dried in air at room temperature. A portion of the solid was subjected to X-ray analysis. The solid had an X-ray powder diffraction pattern characterized by the data shown in Table II.

EXAMPLE III

This Example (DBAP-20) illustrates the preparation of GTex-1 material with medium crystallinity (60%) using tripropylamine as the organic additive. 5.0 grams of Catapal B alumina (pseudoboehmite) was slurried in 15 ml water. To this slurry was added a solution of 9.2 grams of 85% orthophosphoric acid in 12.8 ml water. This mixture was stirred for 5 minutes, and then was allowed to stand at ambient conditions for two hours without agitation. To this mixture was added 5.7 grams of tripropylamine (TPA). This mixture was allowed to stand at ambient conditions for two hours without agitation. To the resulting mixture 4.6 grams of cobalt (III) trisethylenediamine chloride, [Co(en)$_3$]Cl$_3$, complex to form the final reaction mixture. The composition of the final reaction mixture in mole ratio was 1.0 TPA:0.25 [Co(en)$_3$]Cl$_3$:1.0 Al$_2$O$_3$:1.0 P$_2$O$_5$:45 H$_2$O The reaction mixture was stirred at ambient conditions for 4 hours and then placed in a sealed teflon-lined stainless steel pressure vessel and heated at 150° C. for 24 hours. The solid product was recovered by filtration, washed with water, and dried in air at room temperature. A portion of the solid was subjected to X-ray analysis. The solid was impure but the major phase was identified as GTex-1.

EXAMPLE IV

This Example (DBAP-27) is used to show that cobalt (III) trisethylenediamine chloride complex is a necessary ingredient for the synthesis of GTex-1 material. The procedure similar to that of Example I was used except that the cobalt (III) trisethylenediamine chloride complex was not added into the reaction mixture and the total aging time at room temperature was 6 hours. The solid was identified as ALPO-21 by X-ray powder diffraction analysis.

EXAMPLE V

This Example (DBAP-17) is used to show that an organic additive is a necessary ingredient for the synthesis of GTex-1 material. The procedure similar to that of Example I was used except that the TMA was not added into the reaction mixture and the final crystallization time was 20 hours. The solid was identified as condensed phase aluminophosphate (11–500) characterized by having a X-ray powder diffraction pattern shown in Table III.

EXAMPLES VI–XII

This set of Examples is used to demonstrate the effect of the mole ratio (denoted as Co/TBA) of cobalt (III) trisethylenediamine chloride complex to organic additive on the structure and crystallinity of the solid product. In this set of Examples, procedures used in the preparation of Example III were repeated except that tetrabutylammonium hydroxide (TBA) was used to replace TPA, and the Co/TBA ratio was increased from 0.01 to 0.50. The reaction mixtures having the compositions given below were prepared, and were heated at 150° C. for 24 hours. 1.0 TBA:x[Co(en)$_3$]Cl$_3$:1.0 Al$_2$O$_3$:1.0 P$_2$O$_5$:45 H$_2$O, wherein x=0.01, 0.05, 0.10, 0.15, 0.20, 0.25, 0.50. The solid products were subjected to X-ray analysis, and the results are presented in Table IV.

It is seen that at a Co/TBA ratio of 0.01 the major phase in Example VI was VPI-5, an 18-ring aluminophosphate molecular sieve having a very large-pore (12.1 A) unidimensional channel. There is no GTex-1 present in this product. The most striking point is that as the Co/TBA ratio was increased to 0.05, no VPI-5 was formed in Example VII and GTex-1 began to appear. The content of GTex-1 increased with increasing ratio of Co/TBA and appeared to reach a maximum at the Co/TBA ratio of 0.25.

EXAMPLE XIII

In another preparation of GTex-1 with high crystallinity, the procedures of Example I were duplicated, except that the reactive mixture was heated at 125° C. for 96 hours. The resulting solid product (DBAP-37) was found to contain 95% GTex-1.

Determination of Activity for Hydroxylation of Phenol with H$_2$O$_2$ 1. 2 grams of phenol (21 mmole), C$_6$H$_5$OH, 0.2 grams of catalyst, 45 ml of distilled water and 2 grams of 30 wt % hydrogen peroxide, H$_2$O$_2$, (18 mmole) are vigorously mixed in a flask. The reaction is run in a 250 ml three-neck flat-bottom flask fitted with a condenser column. The mixture is heated to the desired temperature.
2. After 5-hours, approximately 2 cc of product is removed and 2 cc of acetone is added. The mixture is analyzed by GC to determine the product composition.
3. The reaction is continued overnight (approximately 15 hrs.).
4. After completion of reaction, the mixture is cooled down to room temperature and 40 ml of acetone is added.
5. The resulting mixture is filtered to remove the catalyst. The mixture is analyzed by GC.

EXAMPLE XIV
Catalyst Activity Comparison

Two titanium silicate (TS-1) samples, one from Georgia Tech. and the other from Utekon were evaluated as the reference catalyst for the hydroxylation of phenol with hydrogen peroxide. Two samples of GTex-1, DBAP-3 and DBAP-41B with high and medium crystallinities, respectively were tested to examine the influence of crystallinity on catalyst performance. The activity and selectivity of all the catalyst samples tested are summarized in Table V.

The TS-1 from Georgia Tech. is almost inactive over the temperature range of 60°–100° C. The TS-1 from Utekon gave about 1.7% conversion of phenol (PH) and hydroquinone (HQ) as the only product at the conditions of 100° C./15 hr. When the reaction product obtained from a run at 60° C. was stored at ambient temperature for over a month period, the phenol conversion went up to 17.4% and the selectivities to catechol (CT) and HQ were 27.5% and 72.5%, respectively. As reported by ENI TS-1 exhibited 25% PH conversion and the ratio of CT to HQ was about 1:1.

DBAP-3 showed PH conversions up to 7.4% at 60°–100° C./15 hr, and the selectivities to catechol (CT) and HQ were 14.4% and 85.6%, respectively. The ratio of CT to HQ was about 1:5.9–7.9. DBAP-41B gave higher PH conversions than DBAP-3, and the ratio of CT to HQ was 1:1.3–2.1. The Co(en)$_3$(H$_2$PO$_4$)$_3$ used in the synthesis of GTex1 gave PH conversion of 0.2%, while, DBAP-41B showed 7.0% at 80° C./15 hr. It is also noted that the cobalt amine complex gave vastly different selectivity ratio of CT to HQ about 3:1. The results suggest that the active center for hydroxylation reaction is not the cobalt amine complexes located on the exterior surface of the GTex1 crystallites. Therefore, GTex1 is an effective catalyst for PH hydroxylation, and may prove that the activity and selectivity of GTex-1 is as good as the TS-1 zeolite.

TABLE I-A

XRD OF DBAP24
SAMPLE I.D.: 052-94-2300-000

| 2θ | D, (Å) | 100 × I/Io |
|---|---|---|
| 6.133 | 14.398 | 22 |
| 8.303 | 10.641 | 8 |
| 8.985 | 9.835 | 62 |
| 12.289 | 7.197 | 18 |
| 13.228 | 6.688 | 4 |
| 17.166 | 5.162 | 4 |
| 18.031 | 4.916 | 100 |
| 18.479 | 4.797 | 14 |
| 20.841 | 4.259 | 7 |
| 21.007 | 4.226 | 8 |
| 22.298 | 3.984 | 4 |
| 23.859 | 3.727 | 8 |
| 24.367 | 3.650 | 4 |
| 25.085 | 3.547 | 4 |
| 26,493 | 3.362 | 7 |

Texaco R&D Beacon

TABLE I-B

XRD OF DBAP24(dry)

| 2θ | d, (Å) | 100 × I/Io |
|---|---|---|
| 8.450 | 10.456 | 4 |
| 9.100 | 9.710 | 36 |
| 12.873 | 6.872 | 9 |
| 17.163 | 5.163 | 5 |
| 18.128 | 4.890 | 100 |
| 46.150 | 1.965 | 5 |
| 56.075 | 1.639 | 5 |

TABLE I-C

XRD OF DBAP24S (Wet)

| 2θ | d, (Å) | 100 × 0/Io |
|---|---|---|
| 8.400 | 10.518 | 9 |
| 8.625 | 10.244 | 43 |
| 9.128 | 9.681 | 40 |
| 12.910 | 6.852 | 17 |
| 16.640 | 5.323 | 4 |
| 17.203 | 5.151 | 71 |
| 18.155 | 4.882 | 100 |
| 18.595 | 4.768 | 5 |
| 19.800 | 4.480 | 5 |
| 20.975 | 4.232 | 4 |
| 21.335 | 4.161 | 5 |
| 21.815 | 4.071 | 5 |
| 22.020 | 4.033 | 4 |
| 23.970 | 3.710 | 5 |
| 25.830 | 3.447 | 6 |
| 25,885 | 3.439 | 6 |

TABLE I-C-continued

XRD OF DBAP24S (Wet)

| 2θ | d, (Å) | 100 × O/Io |
|---|---|---|
| 34.650 | 2.587 | 5 |
| 46.150 | 1.965 | 6 |
| 52.993 | 1.727 | 9 |
| 53.160 | 1.72 | 6 |
| 56.070 | 1.639 | 5 |

TABLE IV

RESULTS OF XRD ANALYSIS

| Example | Sample Code No. | Co/TBA mole ratio | Product by XRD |
|---|---|---|---|
| VI | DBAP8 | 0.01 | VPI-5 (70% U) |
| VII | DBAP9 | 0.05 | GTex-1 (0.5%) CPA, U |
| VIII | DBAP10 | 0.10 | GTex-1 (1%) CPA, U |
| IX | DBAP11 | 0.15 | GTex-1 (3%) CPA, U |
| X | DBAP12 | 0.20 | GTex-1 (6%) CPA, U |
| XI | DBAP13 | 0.25 | GTex-1 (10%) CPA, U |
| XII | DBAP14 | 0.50 | GTex-1 (5%) CPA, U |

U: Unknown phase
CPA: condensed phase aluminophosphate (11–500)

TABLE V

SUMMARY OF HYDROXYLATION OF PHENOL

| CATALYST CODE | CATALYST TYPE | TEMP. °C. | TIME HR. | PH CONV. % | SEL. CT % | SEL. HQ % |
|---|---|---|---|---|---|---|
| 052-94-2390-000 | TS-1 (FT-448) | 100 | 15 | 0.3 | 0 | 100 |
|  |  | 80 | 15 | 0 | — | — |
| 052-92-2090-000 | TS-1 (Utekon) | 60 | 15 | 7.4* | 27.5 | 72.4 |
|  |  | 100 | 15 | 1.7 | 0 | 100 |
| 052-94-2302-000 | DBAP-3 (Co(en)₃) | 100 | 15 | 7.4 | 14.4 | 85.6 |
|  |  | 80 | 15 | 4.5 | 11.2 | 88.7 |
|  |  | 60 | 15 | 1.1 | 0 | 100 |
| 052-94-2303-000 | DBAP-41B | 100 | 15 | 9.8 | 22.1 | 67.8 |
|  |  | 80 | 15 | 7.0 | 43.7 | 56.3 |
|  |  | 60 | 15 | 1.1 | 43.4 | 56.6 |
| 052-94-2355-000 | [Co(en)₃](HPO₄)₃ | 80 | 15 | 0.2 | 74.8 | 25.1 |

*2 g $H_2O_2$ added when temperature reached 60° C., long storage time.

TABLE II

XRD OF OFDBAP3
SAMPLE I.D.: 052-94-2300-000

| 2θ | d, (Å) | 100 × I/Io |
|---|---|---|
| 8.270 | 10.683 | 10 |
| 8.516 | 10.375 | 28 |
| 8.964 | 9.877 | 58 |
| 12.428 | 7.117 | 4 |
| 17.146 | 5.167 | 12 |
| 17.991 | 4.926 | 100 |
| 20.254 | 4.381 | 7 |
| 21.106 | 4.206 | 8 |
| 21.480 | 4.134 | 6 |
| 22.616 | 3.928 | 12 |

Texaco R&D-Beacon

TABLE III

XRD OF CONDENSED ALUMINOPHOSPHATE (11–500)

| 2θ | d, (Å) | 100 × I/Io |
|---|---|---|
| 17.703 | 5.01 | 1 |
| 21.783 | 4.08 | 100 |
| 28.240 | 3.16 | 10 |
| 35.773 | 2.51 | 20 |

EXAMPLE XV

Example XV (DBAP-40) illustrates the synthesis of optically active GTex-1 with high crystallinity (98%). 5.0 grams of Catapal B alumina (pseudoboehmite) was slurried in 9.0 ml water. To this slurry was added a solution of 9.2 grams of 85% orthophosphoric acid in 7.9 ml water. This mixture was stirred for 5 minutes, and then was allowed to stand at ambient conditions for 2 hours without agitation. To this mixture was added 14.5 grams of 25% aqueous solution of tetramethylammonium hydroxide (TMA). This mixture was allowed to stand at ambient conditions for 2 hours without agitation. To the resulting mixture was added 4.6 grams of the dextro isomer of cobalt (III) trisethylenediamine chloride, d-[Co(en)₃]Cl₃, to form the final reaction mixture. The composition of the final reaction mixture in mole ratio was 1.0 TMA:0.25 d-[Co(en)₃]Cl₃:1.0 Al₂O₃:1.0 P₂O₅:45 H₂O.

Figure 1:
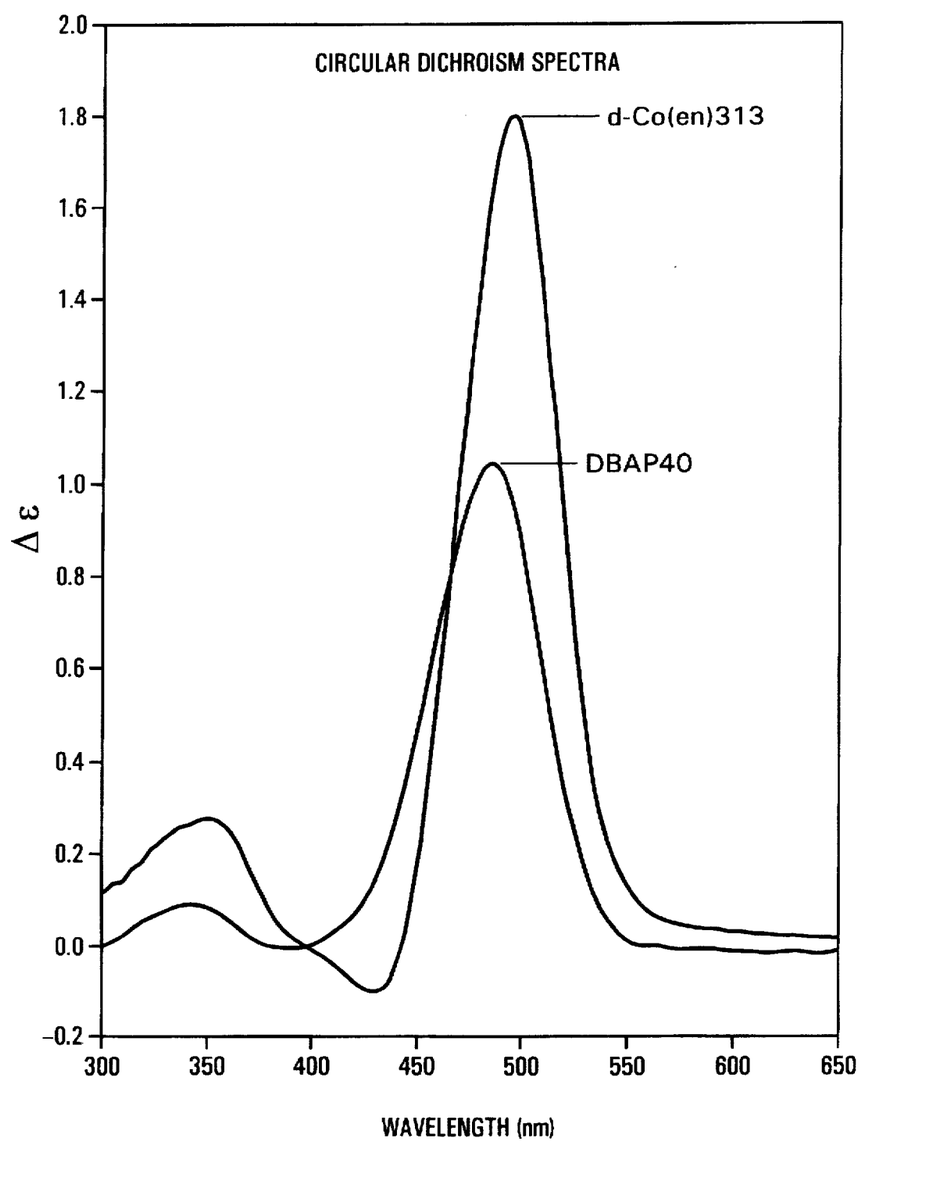
The drawing represents a comparison of the circular dichroism spectra of DBAP-40, the optically active GTex-1 synthesized in Example XV with that of dextro isomer of cobalt trisethylenediamine chloride (d-[Co(en)$_3$]Cl$_3$)

The reaction mixture was placed in a sealed teflon-lined stainless steel pressure vessel and heated at 150° C. for 72 hours. The solid product was recovered by filtration, washed with water, and dried in air at room temperature. A portion of the solid was subjected to X-ray analysis. Optical activity of the AlPO₄ sample was confirmed by circular dichroism techniques. The circular dichroism spectra of DBAP-40 and d-[Co(en)₃]Cl₃ are compared in FIG. 1. Both samples showed similar peaks. Therefore, DBAP-40 was an optically active aluminophosphate. The solid had an X-ray powder diffraction pattern characterized by the data shown in Table VI.

Preparation of Optically Active GTex-2

EXAMPLE XVI

Example XVI (DBAP-47) illustrates the synthesis of optically active GTex-2 with high crystallinity (99%). 5.0 grams of Catapal B alumina (pseudoboehmite) was slurried in 9.0 ml water. To this slurry was added a solution of 9.2 grams of 85% orthophosphoric acid in 7.9 ml water. This mixture was stirred for 5 minutes, and then was allowed to stand at ambient conditions for 2 hours without agitation. To this mixture was added 14.5 grams of 25% aqueous solution of tetramethylammonium hydroxide (TMA). This mixture was allowed to stand at ambient conditions for 2 hours without agitation. To the resulting mixture was added 4.6 grams of the isomer of cobalt (III) bisdiethylenetriamine chloride, $[Co(dien)_2]Cl_3$, to form the final reaction mixture. The composition of the final reaction mixture in mole ratio was $$1.0\ TMA:0.25\ [Co(dien)_2]Cl_3:1.0\ Al_2O_3:1.0\ P_2O_5:45\ H_2O.$$

The reaction mixture was placed in a sealed teflon-lined stainless steel pressure vessel and heated at 150° C. for 72 hours. The solid product was recovered by filtration, washed with water, and dried in air at room temperature. A portion of the solid was subjected to X-ray analysis. The solid had an X-ray powder diffraction pattern characterized by the data shown in Table VII. Optical activity of the $AlPO_4$ sample was confirmed by circular dichroism techniques.

Preparation of Optically Active GTex-3

EXAMPLE XVII

Example XVII (DBAP-60) illustrates the synthesis of optically active GTex-3 with high crystallinity (94%). 5.0 grams of Catapal B alumina (pseudoboehmite) was slurried in 9.0 ml water. To this slurry was added a solution of 9.2 grams of 85% orthophosphoric acid in 7.9 ml water. This mixture was stirred for 5 minutes, and then was allowed to stand at ambient conditions for 2 hours without agitation. To this mixture was added 14.5 grams of 25% aqueous solution of tetramethylammonium hydroxide (TMA). This mixture was allowed to stand at ambient conditions for 2 hours without agitation. To the resulting mixture was added 4.6 grams of the isomer of cobalt (III) tristriethylenediamine chloride, $[Co(tn)_3]Cl_3$, to form the final reaction mixture. The composition of the final reaction mixture in mole ratio was $$1.0\ TMA:0.25\ [Co(tn)_3]Cl_3:1.0\ Al_2O_3:1.0\ P_2O_5:45\ H_2O.$$

The reaction mixture was placed in a sealed teflon-lined stainless steel pressure vessel and heated at 150° C. for 72 hours. The solid product was recovered by filtration, washed with water, and dried in air at room temperature. A portion of the solid was subjected to X-ray analysis. The solid had an X-ray powder diffraction pattern characterized by the data shown in Table VIII. Optical activity of the $AlPO_4$ sample was confirmed by circular dichroism techniques.

XVIII Determination of Activity for Hydroxylation of Phenol with $H_2O_2$ 1. 2 grams of phenol (21 mmole), $C_6H_5OH$, 0.2 grams of catalyst, 45 ml of distilled water and 2 grams of 30 wt % hydrogen peroxide, $H_2O_2$, (18 mmole) are vigorously mixed in a flask. The reaction is run in a 250 ml three-neck flat-bottom flask fitted with a condenser column. The mixture is heated to the desired temperature.
2. After 5-hours, approximately 2 cc of product is removed and 2 cc of acetone is added. The mixture is analyzed by GC to determine the product composition.
3. The reaction is continued overnight (approximately 15 hrs.).
4. After completion of reaction, the mixture is cooled down to room temperature and 40 ml of acetone is added.
5. The resulting mixture is filtered to remove the catalyst. The mixture is analyzed by GC.

XIX. Catalyst Activity

Two titanium silicate (TS-1) samples, one from Georgia Tech. and the other from Utekon were evaluated as the reference catalyst for the hydroxylation of phenol with hydrogen peroxide. The samples of GTex-2 (DBAP-47), $Co(dien)_2Cl_3$, and $[Co(en)_3](H_2PO_4)_3$ were tested to illustrate the catalytic activity of an optically active layered aluminophosphate. The activity and selectivity of all the catalyst samples tested are summarized in Table IX.

The TS-1 from Georgia Tech. is almost inactive over the temperature range of 60°–100° C. The TS-1 from Utekon gave about 1.7% conversion of phenol (PH) and hydroquinone (HQ) as the only product at the conditions of 100° C./15 hr. When the reaction product obtained from a run at 60° C. was stored at ambient temperature for over a month period, the phenol conversion went up to 17.4% and the selectivities to catechol (CT) and HQ were 27.5% and 72.5%, respectively. As reported by ENI TS-1 exhibited 25% PH conversion and the ratio of CT to HQ was about 1:1.

DBAP-47 showed PH conversions from 5.0% to 16.7% at 60°–100° C./15 hr, and the selectivities to catechol (CT) and HQ were 28.9–56.2% and 71.1–43.8%, respectively. The ratio of CT to HQ was about 1:0.8–2.5. The $Co(en)_3(H_2PO_4)_3$ used in the synthesis of GTex-1 gave PH conversion of 0.2%, and $Co(dien)_2Cl_3$ used in the synthesis of GTex-2 showed 1.4% at 80° C./15 hr. In contrast, the DBAP-47 showed PH conversion of 12.7% at 80° C./15 hr. It is also noted that the cobalt amine complex gave a vastly different selectivity ratio of CT to HQ of about 2.4–3:1. The results suggest that the active center for hydroxylation reaction is not the cobalt amine complexes located on the exterior surface of the GTex-1 crystallites. Therefore, GTex-1 is an effective catalyst for PH hydroxylation, and may prove that the activity and selectivity of GTex-1 is as good as or superior to the TS-1 zeolite.

TABLE VI

XRD OF GTEX-1
SAMPLE I.D.: 052-94-2301-000

| 2θ | d, (Å) | 100 × I/Io |
|---|---|---|
| 8.244 | 10.716 | 100 |
| 8.940 | 9.884 | 7 |
| 12.103 | 7.307 | 5 |
| 12.728 | 6.949 | 22 |
| 13.210 | 6.697 | 11 |
| 13.962 | 6.338 | 16 |
| 14.659 | 6.038 | 16 |
| 14.919 | 5.933 | 15 |
| 16.585 | 5.341 | 54 |
| 17.893 | 4.926 | 14 |
| 19.078 | 4.648 | 4 |
| 20.611 | 4.306 | 18 |
| 20.967 | 4.234 | 18 |
| 21.297 | 4.169 | 6 |
| 21.770 | 4.079 | 32 |

TABLE VI-continued

XRD OF GTEX-1
SAMPLE I.D.: 052-94-2301-000

| 2θ | d, (Å) | 100 × I/Io |
|---|---|---|
| 22.244 | 3.993 | 5 |
| 23.376 | 3.802 | 10 |
| 26.595 | 3.349 | 4 |
| 27.355 | 3.258 | 4 |
| 27.918 | 3.193 | 4 |

Texaco R&D-Beacon

TABLE VII

XRD OF DBAP47, GTex-2

| 2θ | d, (Å) | 100 × I/Io |
|---|---|---|
| 8.445 | 10.4618 | 100.00 |
| 8.700 | 10.1557 | 3.82 |
| 12.418 | 7.1224 | 2.42 |
| 12.810 | 6.9051 | 1.16 |
| 13.995 | 6.3230 | 1.16 |
| 16.830 | 5.2637 | 89.75 |
| 17.330 | 5.1129 | 3.37 |
| 19.608 | 4.5239 | 1.01 |
| 21.150 | 4.1973 | 1.81 |
| 21.395 | 4.1498 | 1.78 |
| 21.905 | 4.0543 | 3.29 |
| 24.528 | 3.6264 | 1.54 |
| 25.305 | 3.5168 | 5.58 |
| 25.540 | 3.4849 | 2.38 |
| 26.800 | 3.3239 | 2.64 |
| 28.083 | 3.1749 | 1.18 |
| 30.695 | 2.9104 | 1.75 |
| 31.353 | 2.8508 | 0.71 |
| 34.193 | 2.6203 | 0.83 |
| 34.720 | 2.5817 | 1.45 |
| 37.488 | 2.3872 | 0.81 |
| 38.870 | 2.3150 | 0.81 |
| 44.530 | 2.0330 | 0.61 |
| 47.458 | 1.9142 | 0.61 |
| 48.940 | 1.8597 | 0.63 |
| 51.885 | 1.7608 | 5.75 |

TABLE VIII

XRD OF DBAP60, GTex-3

| 2θ | d, (Å) | 100 × I/Io |
|---|---|---|
| 8.235 | 10.7281 | 100.00 |
| 10.208 | 8.6590 | 8.25 |
| 10.558 | 8.3727 | 3.90 |
| 11.100 | 7.9647 | 7.81 |
| 12.180 | 7.2608 | 6.57 |
| 12.618 | 7.0100 | 8.54 |
| 14.580 | 6.0705 | 12.7 |
| 15.345 | 5.7696 | 8.54 |
| 16.445 | 5.3861 | 61.56 |
| 17.515 | 5.0594 | 7.39 |
| 19.528 | 4.5422 | 12.52 |
| 20.398 | 4.3504 | 9.31 |
| 20.910 | 4.2449 | 2.61 |
| 22.243 | 3.9936 | 4.31 |
| 23.535 | 3.7771 | 10.77 |
| 23.768 | 3.7407 | 9.63 |
| 24.293 | 3.6610 | 10.94 |
| 24.500 | 3.6394 | 4.86 |
| 25.330 | 3.5133 | 4.21 |
| 25.473 | 3.4940 | 6.57 |
| 26.903 | 3.3114 | 2.06 |
| 27.550 | 3.2351 | 2.78 |
| 28.750 | 3.1027 | 5.81 |
| 31.320 | 2.8537 | 3.41 |
| 31.518 | 2.8363 | 2.14 |
| 31.910 | 2.8023 | 3.80 |
| 32.385 | 2.7623 | 2.95 |
| 33.705 | 2.6570 | 2.53 |
| 38.120 | 2.3588 | 8.25 |
| 39.503 | 2.2794 | 2.06 |
| 45.800 | 1.9796 | 3.70 |
| 54.150 | 1.6924 | 4.00 |

TABLE IX (IV)

SUMMARY OF HYDROXYLATION OF PHENOL

| CATALYST CODE | CATALYST TYPE | TEMP. °C. | TIME HR. | PH CONV. % | SEL. CT % | SEL. HQ % |
|---|---|---|---|---|---|---|
| 052-94-2390 | TS-1 (FT-448) | 100 | 15 | 0.3 | 0 | 100 |
| | | 80 | 15 | 0 | — | — |
| 052-92-2090-000 | TS-1 (Utekon) | 60 | 15 | 7.4* | 27.5 | 72.4 |
| | | 100 | 15 | 1.7 | 0 | 100 |
| 052-94-2441-000 | DBAP-47 (Co(dien)$_2$)-ALPO | 100 | 15 | 16.7 | 47.4 | 52.6 |
| | | 80 | 15 | 12.7 | 56.2 | 43.8 |
| | | 60 | 15 | 5.0 | 28.9 | 71.1 |
| 052-94-2443-000 | Co(dien)$_2$Cl$_3$ | 100 | 15 | 5.2 | 38.5 | 61.5 |
| | | 80 | 15 | 1.4 | 70.5 | 29.4 |
| 052-94-2355-000 | [Co(en)$_3$](HPO$_4$)$_3$ | 80 | 15 | 0.2 | 74.8 | 25.1 |

*2 g H$_2$O$_2$ added when temperature reached 60° C., long storage time.

We claim:

1. A method for synthesizing a novel metal-containing aluminophosphate having a layered structure which comprises:
   a) slurring an aluminum source with water;
   b) adding a phosphorus source and stirring;
   c) allowing the mixture to stand;
   d) adding an organic additive;
   e) allowing the mixture to stand;
   f) adding a cationic transition metal complex;
   g) heating to 80°–250° C. for 20–180 hours; wherein the mole ratio of transition metal complex to organic additive is in the range of 0.1–1.0:1.0.

2. The method of claim 1 wherein the aluminum source is pseudoboehmite and the organic additive is selected from dipropylamine, tripropylamine, tetramethylammonium hydroxide and tetrabutylammonium hydroxide.

3. The method of claim 2 wherein the transition metal complexes are selected from cationic transition metal amine complexes and transition metal amino alcohol complexes.

4. The method of claim 2 wherein the cationic transition metal complex is cobalt (III) trisethylenediamine chloride, [Co(en)3]Cl$_3$.

wherein (en) represents an ethylenediamine ligand.

5. A method as described in claim 1 further comprising the synthesis of an optically active form of the novel layered metal-containing aluminophosphate, wherein the addition of a dextro isomer of a transition metal complex is substituted for the cationic transition metal complex.

6. The method of claim 2 wherein the cationic transition metal is pseudoboehmite and the organic additive is selected from dipropylamine, tripropylamine, tetramethylammonium hydroxide and tetrabutylammonium hydroxide.

7. The method of claim 2 wherein the cationic transition metal complex is selected from dextro isomers of transition metal amine complexes and transition metal amino alcohol complexes or [Co(tn)$_3$]Cl$_3$.

wherein (tn) represents a trimethylenediamine ligand.

8. The process of claim 5 wherein the dextro isomer of a transition metal complex is selected from the group consisting of the dextro isomer of cobalt (III) trisethylenediamine chloride, d-[Co(en)$_3$]Cl$_3$, and the isomer of cobalt(III) bisdiethylenetriamine chloride, [Co(dien)$_2$]Cl$_3$.

9. A metal-containing aluminophosphate having a layered structure, wherein the as-synthesized form can be represented by the general formula:

$$M \cdot Al_3P_4O_{16} \cdot nH_2O$$

wherein M is a transition metal complex ion having a +1, +2, or +3 charge.

10. A composition as described in claim 9 wherein the organic additive is selected from the group consisting of dipropylamine, tripropylamine, tetramethylammonium hydroxide and tetrabutylammonium hydroxide.

11. A composition as described in claim 9 wherein the transition metal complex ions are selected from the group consisting of transition metal amine complex ions and transition metal amino alcohol complex ions.

12. A composition as described in claim 9 wherein the transition metal complex ion is an ion of cobalt (III) trisethylenediamine chloride, [Co(en)$_3$]Cl$_3$.

wherein (en) represents an ethylenediamine ligand.

13. A composition as described in claim 9 wherein M is an dextro isomer of a transition metal complex ion having a +1, +2 or +3 charge.

14. A composition as described in claim 13 wherein the isomer of a transition metal complex ion is selected from ions of a transition metal amine complex and transition metal amino alcohol complex.

15. A composition as described in claim 13 wherein the transition metal complex ion is selected from the group consisting of an ion of the dextro isomer of cobalt (III) trisethylenediamine chloride, d-[Co(en)$_3$]Cl$_3$, the isomer of cobalt (III) bisdiethylenetriamine chloride, [Co(dien)$_2$]Cl$_3$ and the isomer of cobalt(III)trisethylenediamine chloride, [Co(tn)3]Cl$_3$.

wherein (en) represents an ethylenediamine ligand, wherein (dien) represents a diethylenediamine ligand and wherein (tn) represents a trimethylenediamine ligand.

* * * * *